US009277856B2

(12) United States Patent
Kobayashi et al.

(10) Patent No.: US 9,277,856 B2
(45) Date of Patent: Mar. 8, 2016

(54) ILLUMINATION DEVICE AND ENDOSCOPE APPARATUS

(75) Inventors: Eiichi Kobayashi, Tokyo (JP); Takakazu Ishigami, Tokyo (JP)

(73) Assignee: OLYMPUS CORPORATION (JP)

( * ) Notice: Subject to any disclaimer, the term of this patent is extended or adjusted under 35 U.S.C. 154(b) by 972 days.

(21) Appl. No.: 13/152,436

(22) Filed: Jun. 3, 2011

(65) Prior Publication Data

US 2011/0237893 A1  Sep. 29, 2011

Related U.S. Application Data

(63) Continuation of application No. PCT/JP2008/072176, filed on Dec. 5, 2008.

(51) Int. Cl.
*F21V 9/16* (2006.01)
*A61B 1/06* (2006.01)
*A61B 1/07* (2006.01)

(52) U.S. Cl.
CPC ............ *A61B 1/0661* (2013.01); *A61B 1/0653* (2013.01); *A61B 1/07* (2013.01)

(58) Field of Classification Search
CPC ...... A61B 1/06; A61B 1/0638; A61B 1/0661; A61B 1/0669; A61B 1/0676; A61B 1/00096; A61B 1/0125; A61B 1/0653
USPC .......... 356/341, 342; 600/178, 180–182, 310, 600/312, 476–487; 250/458.1
See application file for complete search history.

(56) References Cited

U.S. PATENT DOCUMENTS

| 4,381,148 A | * | 4/1983 | Ulrich et al. ............ 356/213 |
| 2003/0050534 A1 | * | 3/2003 | Kazakevich ............ 600/178 |

(Continued)

FOREIGN PATENT DOCUMENTS

| DE | 10 2006 053487 | 11/2006 |
| DE | 10 2006 053487 | 5/2008 |

(Continued)

OTHER PUBLICATIONS

Chinese Office Action mailed on Mar. 28, 2013 by the State Intellectual Property Office of China in connection with corresponding Chinese Application No. 200880132217.0 with translation.

(Continued)

*Primary Examiner* — Anhtuan T Nguyen
*Assistant Examiner* — Aaron B Fairchild
(74) *Attorney, Agent, or Firm* — Ostrolenk Faber LLP

(57) ABSTRACT

An illumination device (1a) includes a light source section (21) outputting excitation light; a fluorescent member (22) excited by the excitation light to emit illumination light; a first light transmitting section (24) disposed between the light source section (21) and the fluorescent member (22) to guide the excitation light output from the light source section (21) to the fluorescent member (22); and a second light transmitting section (25), which is arranged closer to the distal side than the fluorescent member (22) to guide the illumination light emitted from the fluorescent member (22). According to the invention, it is possible to provide an illumination device and an endoscope apparatus capable of exciting the fluorescent member to radiate illumination light, without directly radiating laser light from the light source section to the outside, even if a bending portion or more distal side than the bending portion is damaged in an insertion part.

16 Claims, 14 Drawing Sheets

(56) References Cited

U.S. PATENT DOCUMENTS

| | | | |
|---|---|---|---|
| 2005/0038317 A1* | 2/2005 | Ratnakar | 600/156 |
| 2007/0149858 A1 | 6/2007 | Ogawa et al. | |
| 2008/0214896 A1 | 9/2008 | Krupa et al. | |
| 2008/0232131 A1* | 9/2008 | Suda | 362/574 |
| 2008/0283770 A1 | 11/2008 | Takahashi | |

FOREIGN PATENT DOCUMENTS

| | | |
|---|---|---|
| JP | 2005-152131 | 6/2005 |
| JP | 2006-026135 | 2/2006 |
| JP | 2006-288535 | 10/2006 |
| JP | 2006-296656 | 11/2006 |
| JP | 2007-020937 | 2/2007 |
| JP | 2007-044350 | 2/2007 |
| JP | 2007-275199 | 10/2007 |
| JP | 2008-284030 | 11/2008 |
| JP | 2008-289712 | 12/2008 |
| WO | WO 2006/038502 | 4/2006 |
| WO | WO 2007/105647 | 9/2007 |

OTHER PUBLICATIONS

Office Action issued by the Japanese Patent Office on Dec. 4, 2012 in connection with corresponding Japanese Patent Application No. 2010-541181.

Translation of Office Action issued by the Japanese Patent Office on Dec. 4, 2012 in connection with corresponding Japanese Patent Application No. 2010-541181.

International Search Report mailed Jan. 27, 2009 in corresponding PCT International Application No. PCT/JP2008/072176.

Search Report issued by European Patent Office on Mar. 3, 2014 in connection with corresponding EP patent application No. 08 878 582.9.

Office Action issued by the Japanese Patent Office on Feb. 23, 2012 in connection with corresponding Japanese Patent Application No. 2007-151591.

Translation of Office Action issued by the Japanese Patent Office on Feb. 23, 2012 in connection with corresponding Japanese Patent Application No. 2007-151591.

* cited by examiner

ILLUMINATION DEVICE AND ENDOSCOPE APPARATUS

This application is a Continuation of International Application No. PCT/JP2008/072176, filed on Dec. 5, 2008, which is related to Japanese Patent Application No. 2007-151591, filed on Jun. 7, 2007, the content of which is incorporated herein by reference in their entirety.

TECHNICAL FIELD

The present invention relates to an illumination device and an endoscope apparatus.

BACKGROUND ART

In order to observe the inside of a subject, such as the inside of a machine structure, in industrial fields, and such as the inside of a patient's body, in medical fields, an endoscope apparatus has conventionally been widely used. Such an endoscope apparatus includes an elongate insertion part having a bending portion capable of being freely bent and a hard distal end on the distal side, and being inserted into a subject, and an observation portion is provided at the tip of the insertion part. Also, the insertion part is inserted into the subject, the bending portion is bent by an operating part on the proximal side, and the orientation of a tip is adjusted, so that a desired observation position can be observed inside the subject by the observation portion at the tip. Meanwhile, the inside of the subject observed by the endoscope apparatus mostly does not have enough brightness to be observed by the observation portion. For this reason, an illumination device for illuminating the inside of the subject is built into the endoscope apparatus.

As such an illumination device, an illumination device including following three constituent elements is proposed (for example, refer to Japanese Unexamined Patent Application, First Publication No. 2006-296656 and Japanese Unexamined Patent Application, First Publication No. 2006-288535). That is, the illumination device includes a light source section provided on the proximal side of an insertion part to output laser light as excitation light, a light guide disposed from a proximal end of the insertion part to the tip to guide the laser light emitted from a light source, and a fluorescent member provided at the tip of the insertion part to emit the laser light guided by the light guide as the excitation light.

SUMMARY OF THE INVENTION

The illumination device related to an aspect of the invention is an illumination device including a light source section outputting excitation light; a fluorescent member excited by the excitation light to emit illumination light; a first light transmitting section disposed between the light source section and the fluorescent member to guide the excitation light output from the light source section to the fluorescent member; and a second light transmitting section guiding the illumination light emitted from the fluorescent member.

Additionally, in the illumination device of the above aspect, the illumination device may further include an insertion part having a bending portion capable of being freely bent on the distal side and inserted into a subject, and the fluorescent member may be provided in proximity to the bending portion located on the distal side, within the insertion part.

Additionally, in the illumination device of the above aspect, the illumination device may further include an insertion part having a bending portion capable of being freely bent on the distal side and inserted into a subject, and the fluorescent member may be provided closer to the proximal side than the bending portion, within the insertion part.

Moreover, the illumination device may further include a bending operating part which controls bending of the bending portion, and the light source section may be provided within the bending operating part.

Furthermore, the illumination device may further include an apparatus body portion provided on the proximal side of the insertion part, and the light source section may be provided within the apparatus body portion.

In addition, in the illumination device of the above aspect, the illumination device may further include an insertion part having a bending portion capable of being freely bent on the distal side and inserted into a subject, and a bending operating part which controls bending of the bending portion, and the fluorescent member may be provided within the bending operating part.

Furthermore, the illumination device may further include an apparatus body portion provided on the proximal side of the insertion part, and the light source section may be provided within the apparatus body portion.

In addition, in the illumination device of the above aspect, the illumination device may further include an apparatus body portion having a housing, and an extending portion connected to the apparatus body portion and extending from the apparatus body portion, and the fluorescent member may be provided within the apparatus body portion.

Additionally, the above illumination device may further include a diffuser plate provided on the distal side of the second light transmitting section to diffuse the illumination light guided to the second light transmitting section.

Additionally, the above illumination device may further include a plurality of sets of illumination portions constituted by the light source section, the fluorescent member, the first light transmitting section, and the second light transmitting section.

Additionally, in the above illumination device, the fluorescent member may be provided with a heat radiation portion which receives and radiates the heat generated in the fluorescent member.

Additionally, the above illumination device may further include an input-side light determining section which determines the amount of the excitation light emitted from the light source section and guided to the first light transmitting section and outputs a detection signal.

Moreover, in the above illumination device, the input-side light determining section may be provided in proximity to the fluorescent member.

Additionally, the above illumination device may further include an output-side light determining section which determines the amount of the illumination light emitted from the fluorescent member and guided to the second light transmitting section and outputs a detection signal.

Additionally, the above illumination device may further include an amplifier provided inside the insertion part to amplify the detection signal and transmit the amplified detection signal to the proximal side of the insertion part.

Additionally, in the above illumination device, the first light transmitting section and the second light transmitting section may be light guides.

Additionally, an endoscope apparatus related to the aspect may include the above illumination device, and an observation portion provided at the tip of the insertion part and capable of observing the inside of the subject.

BEST MODE FOR CARRYING OUT THE INVENTION

One embodiment according to the invention will be described below with reference to FIGS. 1 to 6.

Figure 1:
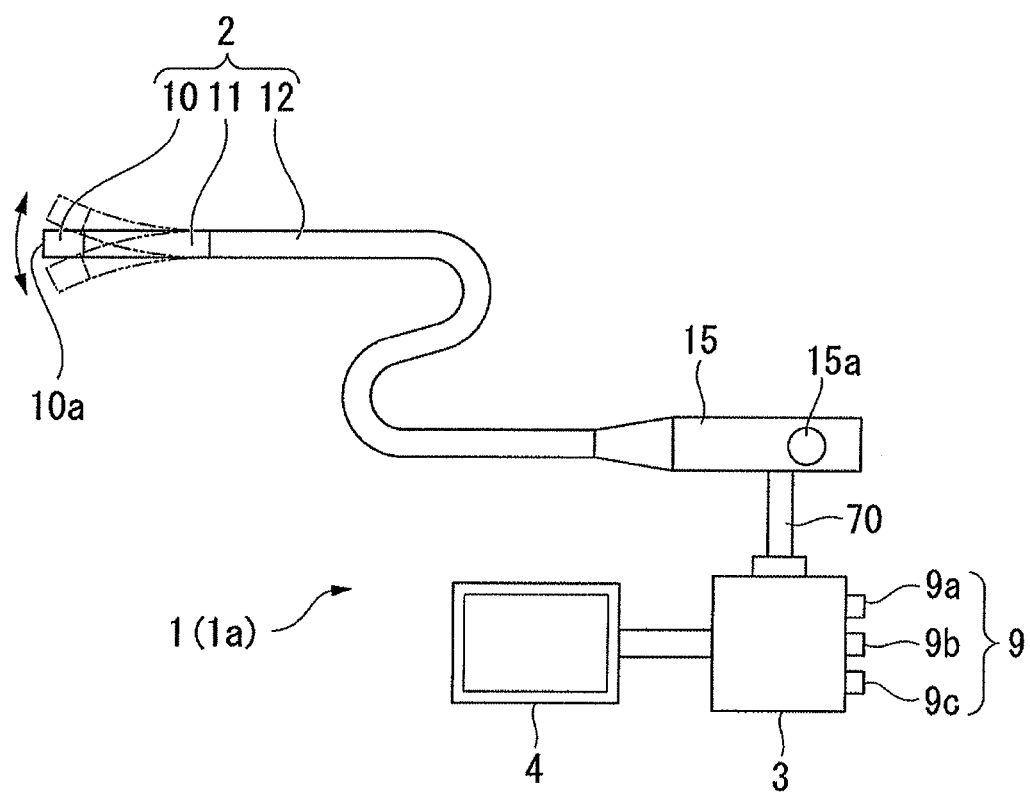
FIG. 1 is an overall schematic view showing an external configuration of an endoscope apparatus of a first embodiment.
Figure 2:
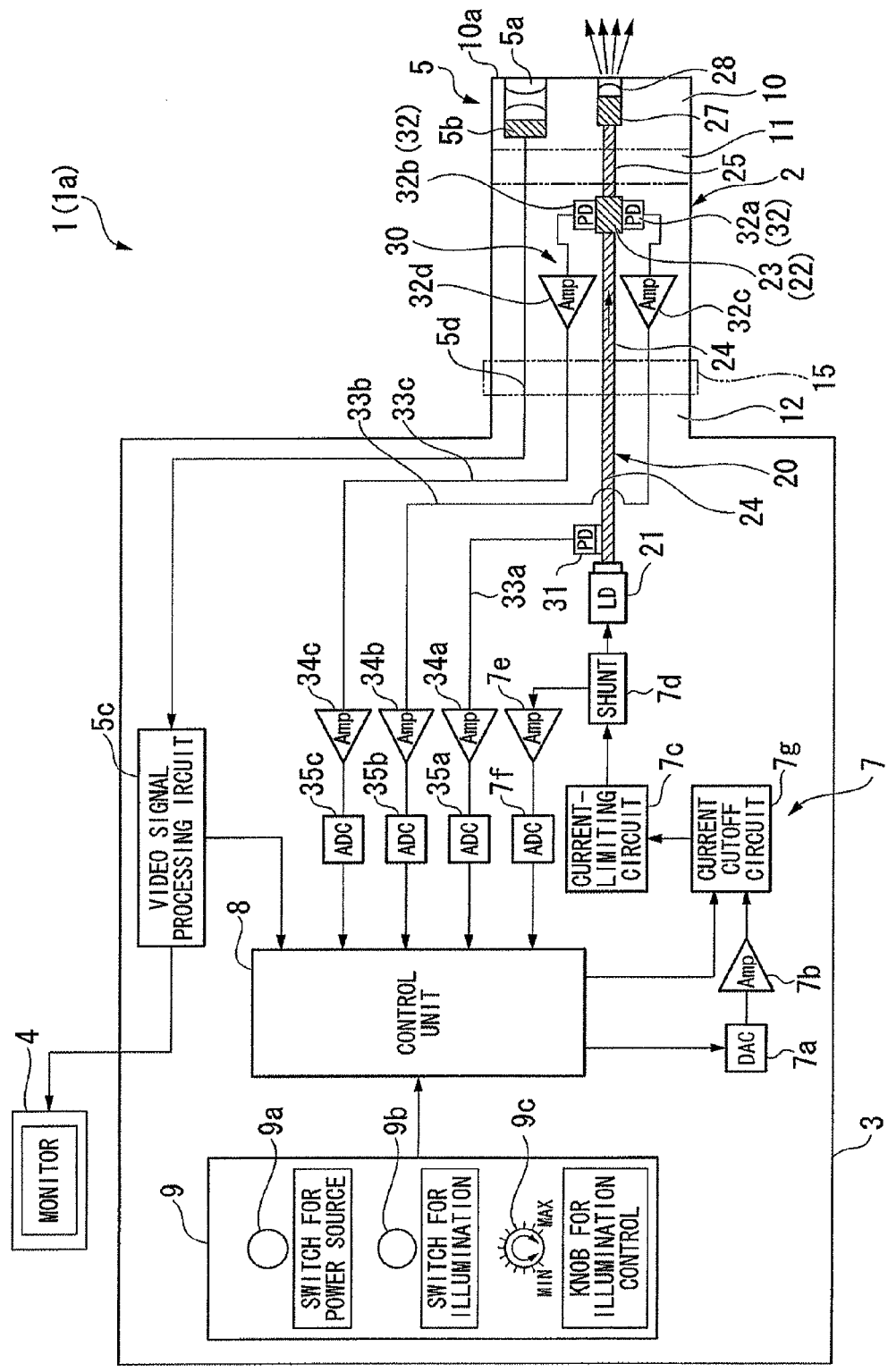
FIG. 2 is an overall configuration view showing an internal configuration of the endoscope apparatus of the first embodiment.

As shown in FIGS. 1 and 2, an endoscope apparatus 1 related to the present embodiment includes an elongate insertion part 2 inserted into a subject, an apparatus body part 3 having a housing provided on the proximal side of the insertion part 2, and a monitor 4 connected to the apparatus body part 3. Additionally, the insertion part 2 and the apparatus body part 3 are provided with an observation portion 5 that observes a subject on the distal side of the insertion part 2, and an illumination portion 20 which illuminates the subject observed by the observation portion 5. Accordingly, the endoscope apparatus 1 has a configuration including an illumination device 1a having the insertion part 2, the illumination portion 20, and a control unit 8 as will be described below. In addition, the apparatus body part 3 and the illumination device 1a are connected together by an extending portion 70 extending from the apparatus body part 3. Hereinafter, respective components will be described in detail.

Figure 3:
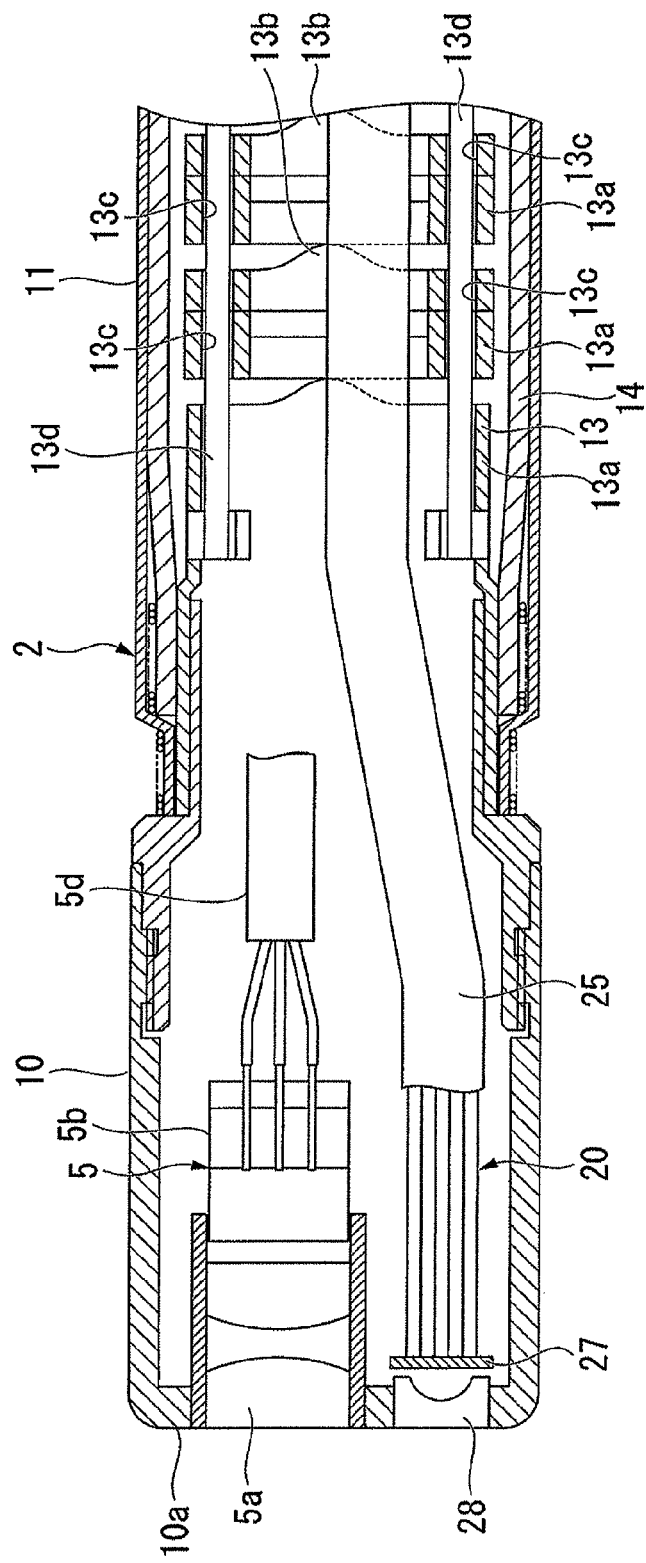
FIG. 3 is a sectional view showing details of a distal end and a bending portion, in an insertion part of the endoscope apparatus of the first embodiment.
Figure 4:
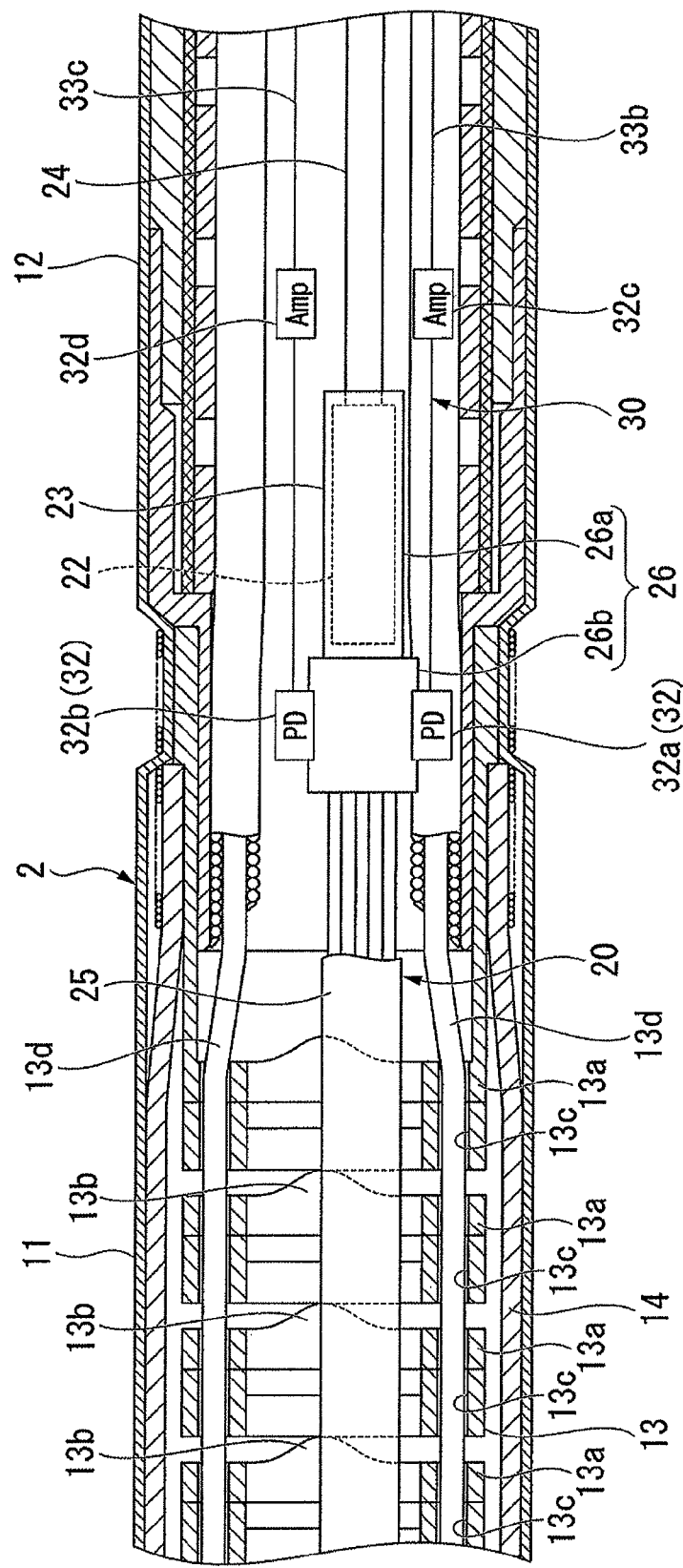
FIG. 4 is a sectional view showing details of the bending portion and a flexible tube portion, in the insertion part of the endoscope apparatus of the first embodiment.
Figure 5:
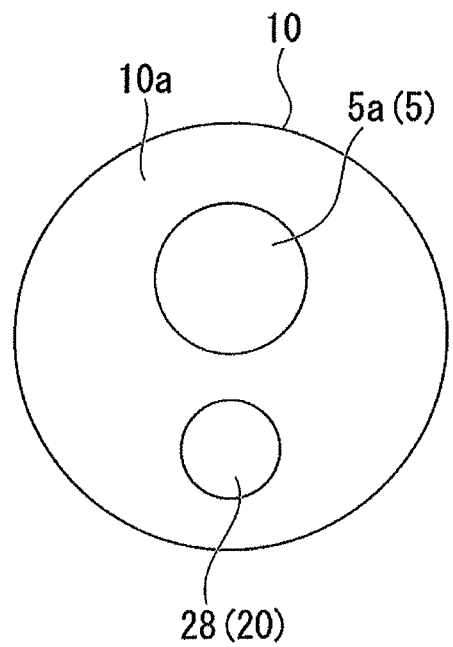
FIG. 5 is a front view of the distal end in the insertion part of the endoscope apparatus of the first embodiment.

As shown in FIG. 1, the insertion part 2 is of a soft type having a hard distal end 10, a bending portion 11 capable of being freely bent by a bending operating part 15 as will be described below, and a flexible tube portion 12 capable of being bent according to the shape of a subject, sequentially from the tip. As shown in FIG. 3, the distal end 10 is formed substantially in a tubular shape having a tip face 10a, and an objective optical system 5a of the observation portion 5 and an optical system 28 for illumination of the illumination portion 20 which will be described below are provided so as to be exposed to the tip face 10a. As shown in FIG. 4, the flexible tube portion 12 is a long, substantially tubular member having flexibility.

Additionally, as shown in FIGS. 3 and 4, the bending portion 11 has a bending tube 13 which is configured such that a plurality of bending pieces 13a are continuously connected together, and an elastic tubular member 14 which is substantially tubular, is disposed so as to cover the outer periphery of the bending tube 13, and is elastically deformable. The bending tube 13 of the bending portion 11 is fixed to the distal end 10 on the distal side and to the flexible tube portion 12 on the proximal side. Additionally, each bending piece 13a which constitutes the bending tube 13 is formed with a pair of convex portions 13b (only one is shown in FIGS. 3 and 4) which protrude arcuately toward the proximal side at two places which face each other in the radial direction. The convex portions 13b abut on the tip of another adjacent bending piece 13a. The positions of the convex portions 13b of each bending piece 13a are set so as to be almost the same in the circumferential direction. For this reason, the bending tube 13 can be bent in a corresponding direction as a whole as the individual bending pieces 13a rotate in almost the same direction about the pair of convex portions 13b in a state where the bending tube 13 is disposed inside the elastic tubular member 14. Additionally, in each bending piece 13a, a pair of through holes 13c is formed at a position corresponding to a direction in which the bending tube 13 is bent, i.e., at an intermediate position of the pair of convex portions 13b, and a pair of operating wires 13d is inserted through the through holes, respectively. In the pair of operating wires 13d, the operating wire on the distal side is fixed to the tip of the bending tube 13, and the operating wire on the proximal side is inserted through the flexible tube portion 12. Then, as shown in FIG. 1, the operating wires are connected to the bending operating part 15 provided at a proximal end of the flexible tube portion 12. The bending operating part 15 is provided with a joy stick 15a. Any one of the pair of operating wires 13d can be pulled by the operation of the joy stick 15a, and thereby, the bending portion 11 can be bent as a whole toward the towed operating wire 13d.

As shown in FIGS. 2 and 3, the observation portion 5 has an objective optical system 5a, a CCD (Charge Coupled Device) 5b, a video signal processing circuit 5c, and a signal cable 5d. Here, the objective optical system 5a is provided so as to be exposed to the distal end 10 of the insertion part 2. The CCD 5b is an imaging device which is provided at the imaging position of the objective optical system 5a inside the distal end 10. The video signal processing circuit 5c is built into the apparatus body part 3. The signal cable 5*d* is disposed at the insertion part 2 to connect together the CCD 5*b* and the video signal processing circuit 5*c*. Also, the observation image of the subject imaged by the objective optical system 5*a* is converted into an electrical signal by the CCD 5*b*, and is transmitted by the signal cable 5*d* as an image signal. The transmitted image signal can be generated as a video signal by the video signal processing circuit 5*c*, be output to the monitor 4 connected to the apparatus body part 3, and be projected as an image.

Additionally, the illumination portion 20 has a laser diode 21, an illumination light generating section 23, a first light guide 24, and a second light guide 25. Here, the laser diode 21 is a light source section which is built into the apparatus body part 3 to output laser light as excitation light. The illumination light generating section 23 is provided inside the insertion part 2, and has a fluorescent member 22. The first light guide 24 is a first light transmitting section disposed between the laser diode 21 and the illumination light generating section 23 inside the insertion part 2. The second light guide 25 is a second light transmitting section disposed from the illumination light generating section 23 to the distal end 10 inside the insertion part 2. The laser diode 21 can output monochromatic laser light with an amount according to the intensity of current supplied, and can output blue laser light in the present embodiment.

Additionally, in the present embodiment, the first light guide 24 is a single fiber, and, the second light guide 25 is a multi-fiber. Additionally, the illumination light generating section 23 is arranged at a position close to the bending portion 11 on the proximal side of the bending portion 11, i.e., at the tip inside the flexible tube portion 12, and has the fluorescent member 22 and a case 26 which receives the fluorescent member 22 therein. The fluorescent member 22 is formed from a fluorescent substance which is excited by laser light to emit white light. The case 26 has a case body 26*a* which receives the fluorescent member 22, and a ferrule 26*b* which is externally fitted to the distal side of the case body 26*a*. A connection port 26*c* to which the tip of the first light guide 24 is connected is provided on the proximal side of the case body 26*a*. Thereby, the internal fluorescent member 22 can be irradiated with the laser light from the laser diode 21 guided by the first light guide 24. Additionally, the distal side of the case body 26*a* opens and communicates with the ferrule 26*b*. The distal side of the ferrule 26*b* is externally fitted to a proximal end of the second light guide 25. For this reason, the illumination light which is excited by the laser light and emitted from the fluorescent member 22 enters the proximal end of the second light guide 25 through the inside of the ferrule 26*b*, and is guided to the distal side.

In addition, the first light guide 24 is not limited to the single fiber, and may be resin. For example, in a case where the fluorescent member 22 has a fluorescent material provided so as to segregate in the resin, a portion of which the content ratio of the fluorescent material is low can be regarded as the first light guide 24.

Here, the first light guide made of resin is inexpensive as compared to a fiber made of quartz or the like. In addition, even in a case where the first light guide is damaged due to an external stress, damage to the first light guide can be further suppressed by deformation of resin, by using resin with a low Young's modulus as compared to quartz.

Additionally, the illumination portion 20 has a diffuser plate 27 which is provided at the tip of the second light guide 25 inside the distal end 10 of the insertion part 2, and an optical system 28 for illumination which is provided on more distal side than the diffuser plate 27 and is exposed to the tip face 10*a* of the distal end 10. The diffuser plate 27 is, for example, a glass plate whose surface has been subjected to roughening, or in which a particulate reflector is included, and can diffuse the illumination light guided by the second light guide 25 and emitted from the tip thereof and transmit the illumination light therethrough. Additionally, the optical system 28 for illumination can converge and shape the illumination light transmitted through the diffuser plate 27 to radiate the illumination light to the outside.

Additionally, as shown in FIG. 2, a light source driving unit 7 which supplies current to the laser diode 21, and a control unit 8 which controls the amount of the electric current supplied from the light source driving unit 7 are built into the apparatus body part 3, and a control panel 9 is connected to the control unit 8. The control panel 9 is provided with a switch 9*a* for a power source which turns on/off a power source of the overall apparatus, a switch 9*b* for illumination which performs ON/OFF of the illumination light by the illumination portion 20, and a knob 9*c* for illumination control which performs adjustment of the amount of the illumination light in the state where the switch 9*b* for illumination is turned on. Also, in a case where the switch 9*a* for a power source is turned on, ON/OFF of illumination by the illumination portion 20, and adjustment of the amount of light can be manually performed via the control unit 8 by the operation of the control panel 9.

The light source driving unit 7 has a DA converter 7*a*, an amplifier 7*b*, and a current-limiting circuit 7*c*. Here, the DA converter 7*a* DA-converts a current command value output from the control unit 8. The amplifier 7*b* amplifies the current command value DA-converted by the DA converter 7*a*. The current-limiting circuit 7*c* supplies current to the laser diode 21 with a corresponding amount of current on the basis of the amplified current command value. Also, the laser diode 21 outputs laser light with an amount according to a current command value (the amount of current). In addition, since a shunt 7*d* serving as a current determining portion is interposed between the current-limiting circuit 7*c* and the laser diode 21, the amount of current supplied to the laser diode 21 from the current-limiting circuit 7*c* is determined, and is output as a detection signal. The output detection signal is input to the control unit 8 via an amplifier 7*e* and an AD converter 7*f* and the control unit 8 performs feedback control on the basis of the amount of current determined.

Additionally, a current cutoff circuit 7*g* is interposed between the current-limiting circuit 7*c* and the amplifier 7*b*. The control unit 8 can output a cutoff signal to the current cutoff circuit 7*g*, and the current cutoff circuit 7*g* can cut off input of the current command value to the current-limiting circuit 7*c*, on the basis of the cutoff signal, and stop supply of the current to the laser diode 21.

Additionally, as shown in FIG. 2, the insertion part 2 and the apparatus body part 3 are provided with the light determining portion 30 which determines the amount of laser light and illumination light in the illumination portion 20. In more detail, the light determining portion 30 includes an input-side light determining section 31 which determines the amount of laser light emitted from the laser diode 21, and outputs a detection signal, and an output-side light determining section 32 which determines the amount of illumination light emitted from the fluorescent member 22, and outputs a detection signal. The input-side light determining section 31 is a photodiode which can detect the amount of light with almost the same wavelength as the laser light, and can be provided at the outer peripheral surface of the proximal end of the first light guide 24 to detect the amount of laser light by the leaked light which leaks to the outer peripheral surface from the inside.

The detection signal output from the input-side light—determining section 31 is transmitted by a signal line 33a, is amplified by an amplifier 34a, is AD-converted by an AD converter 35a, and is input to the control unit 8.

Figure 6:
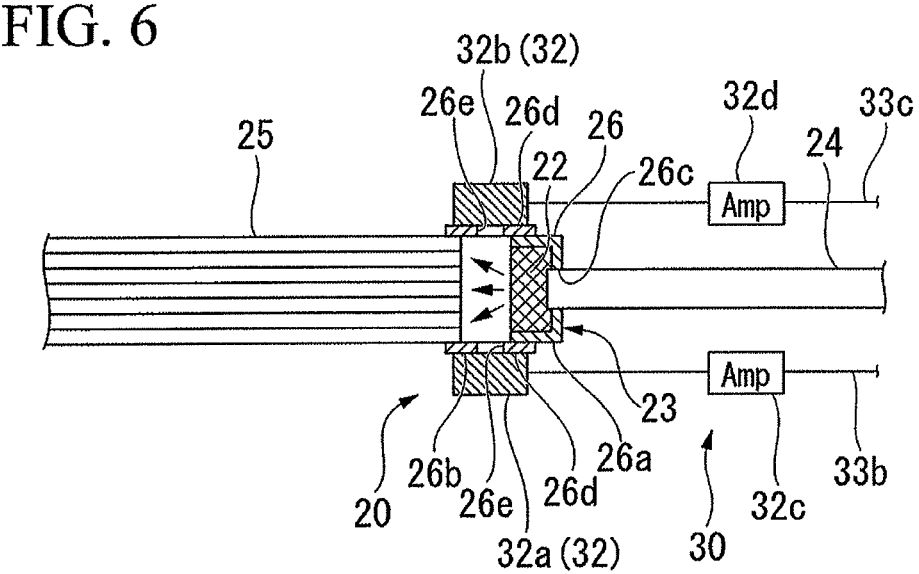
FIG. 6 is a sectional view showing details of an illumination light generating section, in the endoscope apparatus of the first embodiment.

Additionally the output-side light determining section 32 is provided in the vicinity of the fluorescent member 22 inside the insertion part 2. The output-side light determining section 32 has a first optical sensor 32a that is a photodiode which determines the amount of light with almost the same wavelength as the laser light in the illumination light. The output-side light determining section 32 further has a second optical sensor 32b that is a photodiode which determines the amount of light with wavelengths other than that of the laser light in the illumination light. As shown in FIG. 6, the first optical sensor 32a and second optical sensor 32b of the output-side light determining section 32 can detect a portion of the illumination light which leaks to the outside from a detection port 26e formed so as to communicate from the outside to the inside, in a lateral face 26d of the case 26 of the illumination light generating section 23. Detection signals output from the first optical sensor 32a and the second optical sensor 32b are amplified by the amplifiers 32c and 32d, respectively, provided in proximity to each other inside the insertion part 2. Thereafter, the detection signals are transmitted by signal lines 33b and 33c disposed at the insertion part 2, and are further amplified by amplifiers 34b and 34c inside the apparatus body part 3. Simultaneously, the detection signals are AD-converted by the AD converters 35b and 35c, and are input to the control unit 8.

Next, the operation of the endoscope apparatus 1 of this embodiment will be described. As shown in FIGS. 1 and 2, when the switch 9a for a power source and the switch 9b for illumination of the control panel 9 are turned on, the control unit 8 outputs to the light source driving unit 7 a current command value corresponding to the knob 9c for illumination control. Thereafter, the light source driving unit 7 supplies to the laser diode 21 current of an intensity corresponding to the input current command value. For this reason, laser light is output with an amount corresponding to the amount of current supplied to the laser diode 21, and is guided to the distal side by the first light guide 24, and the fluorescent member 22 is irradiated with the laser light. Here, the amount of the laser light emitted from the laser diode 21 and entered into the first light guide 24 is determined by the input-side light determining section 31, and is input to the control unit 8. For this reason, the control unit 8 can detect the existence/non-existence of degradation or damage to the laser diode 21 on the basis of a detection result.

Additionally, the fluorescent member 22 is irradiated and excited with the laser light guided by the first light guide 24, and the fluorescent member 22 emits the illumination light with an amount corresponding to the amount of laser light. Here, as shown in FIG. 6, most of the illumination light emitted from the fluorescent member 22 directly enters into the second light guide 25 located on the distal side, or is reflected from the case 26 and enters into the second light guide 25. On the other hand, a portion of the illumination light enters into the detection port 26e, and is determined by the first optical sensor 32a and second optical sensor 32b of the output-side light determining section 32. Then, individual detection results from the output-side light determining section 32 are input to the control unit 8. For this reason, on the basis of the detection results, the control unit 8 can detect the existence/non-existence of degradation or damage to the fluorescent member 22, and can detect the existence/non-existence of degradation or damage to the laser diode 21 or the first light guide 24. Particularly, the output-side light determining section 32 is constituted by the first optical sensor 32a and the second optical sensor 32a, and determines the amount of the illumination light which is divided into the amount of light with almost the same wavelength as the laser light and the amount of light with wavelengths other than that of the laser light in the illumination light. Through such detection, more in detail, the existence/non-existence of degradation or damage is detected on the basis of the detection results. In a case where an abnormality is recognized, a cause can be specified in detail.

Additionally, the illumination light enters into the second light guide 25 is guided up to the distal side, and is shaped by the optical system 28 for illumination so as to illuminate the outside. For this reason, an image inside a subject can be favorably received by the observation portion 5, using the reflected light of the above illumination light, and the insertion part 2 is inserted into the subject while checking an observation image displayed on the monitor 4, thereby enabling detailed observation. Additionally, during observation, the bending portion 11 of the insertion part 2 can be bent in a predetermined direction by operating the joy stick 15a of the bending operating part 15. Thereby, the orientation of the objective optical system 5a of the observation portion 5 can be adjusted to observe the inside of a subject in a wide range. In this case, as the diffuser plate 27 is provided at the tip of the second light guide 25, the illumination light is further diffused and illuminated to the outside. As a result, a wider range can be effectively illuminated and observed.

Here, when the insertion part 2 is inserted into a subject, the bending portion 11 and the distal end 10 of the insertion part 2 may be damaged due to the insertion resistance received from the subject. Depending on the degree of damage, there is a possibility that the second light guide 25, the diffuser plate 27, or the optical system 28 for illumination, which are disposed inside the bending portion 11 or the distal end 10, in the illumination portion 20 may be damaged. On the other hand, the fluorescent member 22 or the first light guide 24 in the illumination portion 20 is located closer to the proximal side than the bending portion 11. Accordingly, even if the bending portion 11 and the distal end 10 have been damaged, any corresponding damage is suppressed. For this reason, the laser light emitted from the laser diode 21 is prevented from leaking to the outside from a damaged part until the fluorescent member 22 is irradiated with the laser light as a result of the first light guide 24 or the fluorescent member 22 being damaged.

Additionally, as described above, there is a possibility that the second light guide 25, the diffuser plate 27, or the optical system 28 for illumination may be damaged in conjunction with damage to the bending portion 11 or the distal end 10. However, since these are disposed closer to the distal side than the fluorescent member 22, the illumination light only leaks to the outside, and an influence on a subject is suppressed. Here, the fluorescent member 22 is provided in proximity to the bending portion 11, and is thereby arranged as close to the distal side as possible within a range closer to the proximal side than the bending portion 11. For this reason, the length of the second light guide 25 to which the illumination light is guided can be minimized. Thereby, attenuation of the illumination light guided by the second light guide 25 can be suppressed to the minimum.

Moreover, in the insertion part 2, the CCD 5b of the observation portion 5 is built into the distal end 10. The heat radiation conditions of the fluorescent member 22 can be made suitable not by disposing the fluorescent member 22 at the distal end 10 which will be at almost the same position as the CCD 5b in the axial direction of the insertion part 2, but by disposing the fluorescent member 22 at the flexible tube portions 12 with few built-in components. As a result, degradation of the fluorescent member 22 and decline in the conversion efficiency of the illumination light from the laser light can be suppressed.

Additionally, the CCD 5b built into the distal end 10 is at a position different from the fluorescent member 22 in the axial direction of the insertion part 2. Accordingly, the CCD 5b can suppress the influence of the heat received from the fluorescent member 22. As a result, the noise generated in the CCD 5b can be reduced.

Additionally, by including the input-side light determining section 31 or the output-side light determining section 32 as described above, the state of laser light or illumination light can be quantitatively estimated, and the existence/non-existence of abnormalities of individual components of the illumination portion 20 can be detected. For this reason, an external subject can be prevented from continuing to be illuminated with the illumination light in an abnormal state. Here, since the output-side light determining section 32 is provided in the vicinity of the fluorescent member 22 to detect illumination light, the illumination light can be determined in the state where the illumination light is not attenuated immediately after emission from the fluorescent member 22. Accordingly, the amount of the illumination light can be accurately evaluated. Additionally, the detection results of the output-side light determining section 32 are amplified by the individual amplifiers 32c and 32d inside the insertion part 2, respectively, are then transmitted to the apparatus body part 3 by the signal lines 33b and 33c, and are input to the control unit 8. For this reason, also in the elongate insertion part 2, the individual detection signals of the output-side light determining section 32 can be transmitted to the proximal side, while suppressing an increase in noise and suppressing a decrease in output. Accordingly, the control unit 8 can perform the detection of occurrences of an abnormality and the determination of a cause more accurately.

Figure 7:
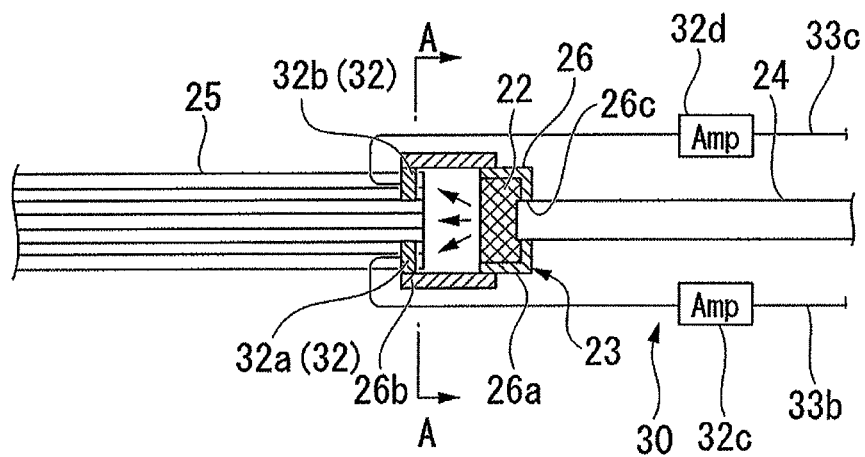
FIG. 7 is a sectional view showing details of an illumination light generating section, in an endoscope apparatus of a first modification of the first embodiment.
Figure 8:
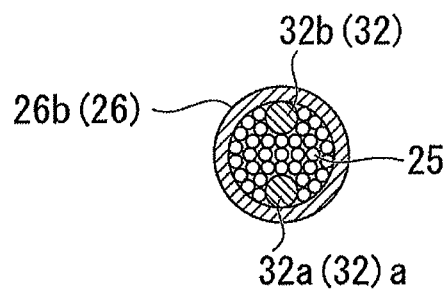
FIG. 8 is a sectional view at a cutting line A-A of FIG. 7.
Figure 9:
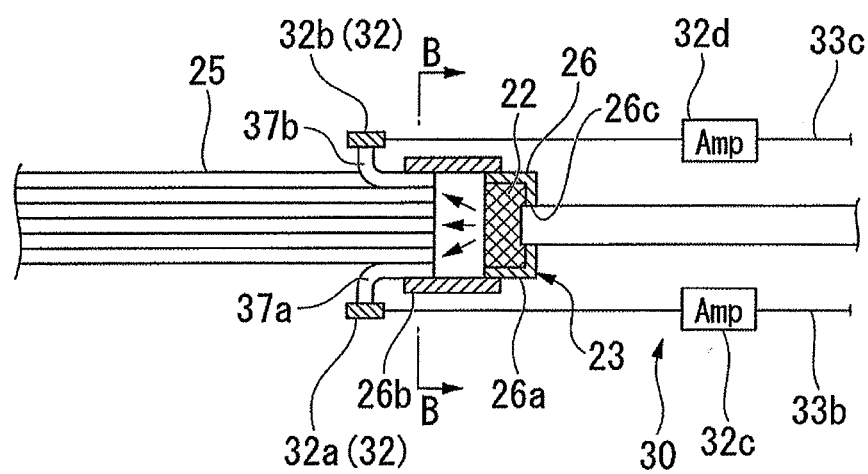
FIG. 9 is a sectional view showing details of an illumination light generating section, in an endoscope apparatus of a second modification of the first embodiment.
Figure 10:
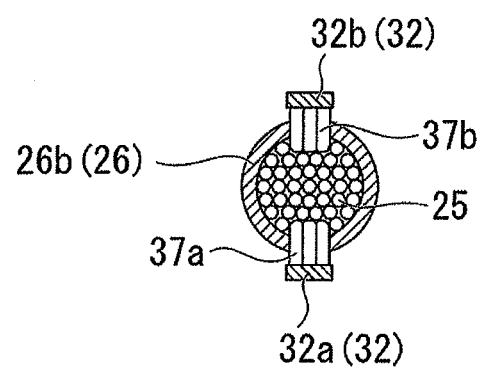
FIG. 10 is a sectional view at a cutting line B-B of FIG. 9.

In addition, in the above, the output-side light determining section 32 determines illumination light from the detection port 26e provided in the case 26. However, the invention is not limited thereto. FIGS. 7 and 8 show a first modification of this embodiment, and FIGS. 9 and 10 show a second modification of this embodiment. As shown in FIGS. 7 and 8, in the present modification, the first optical sensor 32a and second optical sensor 32b of the output-side light determining section 32 are fitted into a portion of an opening on the distal side to which the proximal end of the second light guide 25 is fitted, in the ferrule 26b of the case 26. For this reason, the illumination light emitted from the fluorescent member 22 is reflected directly or from the case 26, enters into the second light guide 25, and is determined by the output-side light determining section 32.

Additionally, as shown in FIGS. 9 and 10, in the present modification, proximal ends of fiber bundles 37a and 37b are fitted into a portion of an opening on the distal side to which the proximal end of the second light guide 25 is fitted, in the ferrule 26b of the case 26. Simultaneously, the first optical sensor 32a and second optical sensor 32b of the output-side light determining section 32 are optically connected to the tips of the individual fiber bundles. For this reason, the illumination light emitted from the fluorescent member 22 is reflected directly or by the case 26, and enters into the second light guide 25. Simultaneously, the illuminating light enters into the individual fiber bundles 37a and 37b, and is determined by the first optical sensor 32a and second optical sensor 32b of the output-side light determining section 32. In addition, in the above embodiment and the modification thereof, the output-side light determining section 32 directly determines the illumination light emitted to the inside of the case 26. However, the invention is not limited thereto. The output-side light determining section 32 may be provided at the peripheral surface of the second light guide 25, and determines the amount of illumination light according to the leaked light of the second light guide 25.

Figure 11:
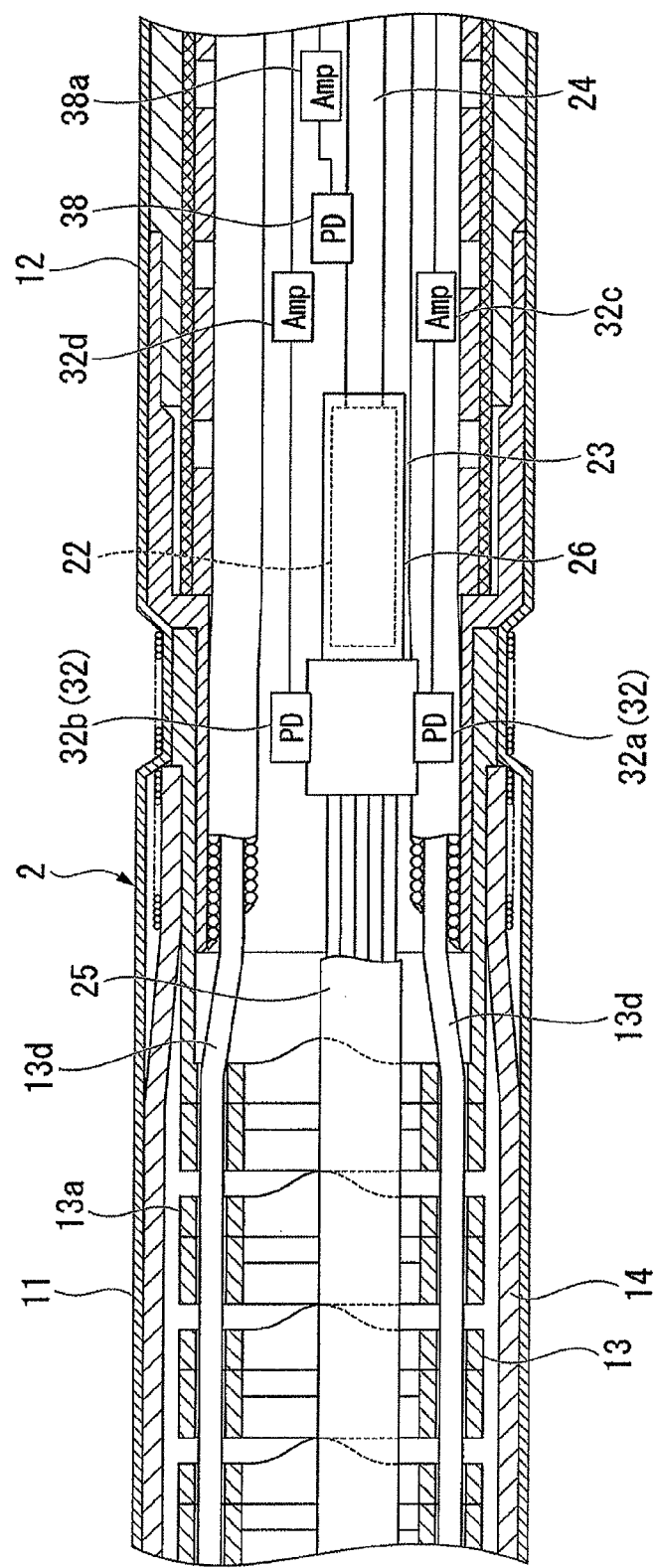
FIG. 11 is a sectional view showing details of a bending portion and a flexible tube portion, in an insertion part of an endoscope apparatus of a third modification of the first embodiment.

Additionally, the input-side light determining section 31 is provided at the outer peripheral surface of the proximal end of the first light guide 24 to detect the amount of laser light according to the leaked light of the first light guide 24. However, the invention is not limited thereto. The input-side light determining section 31 may be of a type which is built into the laser diode 21, or may be of a type which performs detection on the distal side of the first light guide 24. In FIG. 11, as a third modification of this embodiment, the input-side light determining section 38 is configured so as to be provided at the outer peripheral surface of the tip of the first light guide 24. In this way, by determining the amount of laser light by the leaked light of the outer peripheral surface of the first light guide 24, any damage to a part closer to the proximal side than the position where the input-side light determining section 38 is provided can be determined in the first light guide 24. Particularly, by providing the input-side light determining section 38 at the outer peripheral surface of the tip of the first light guide 24, the existence/non-existence of degradation or damage can be detected over almost the entire range of the first light guide 24. Additionally, the following effects can be exhibited, for example, by using a plurality of optical sensors as the input-side light determining section, and arranging the optical sensors at the outer peripheral surfaces of the proximal and distal ends of the light guide 24. That is, as to whether occurrence of an abnormality is caused by the laser diode 21 or the first light guide 24, the cause can be specified in more detail depending on the detection results of the input-side light determining section. In addition, as described above, the following effects can be exhibited even in a case where the input-side light determining section 38 is provided at the outer peripheral surface of the tip of the first light guide 24. That is, a decrease in output and an increase in noise can be suppressed by amplifying detection signals by amplifiers 38a provided at positions close to each other inside the insertion part 2, and then transmitting the detection signals to the proximal side.

Figure 12:
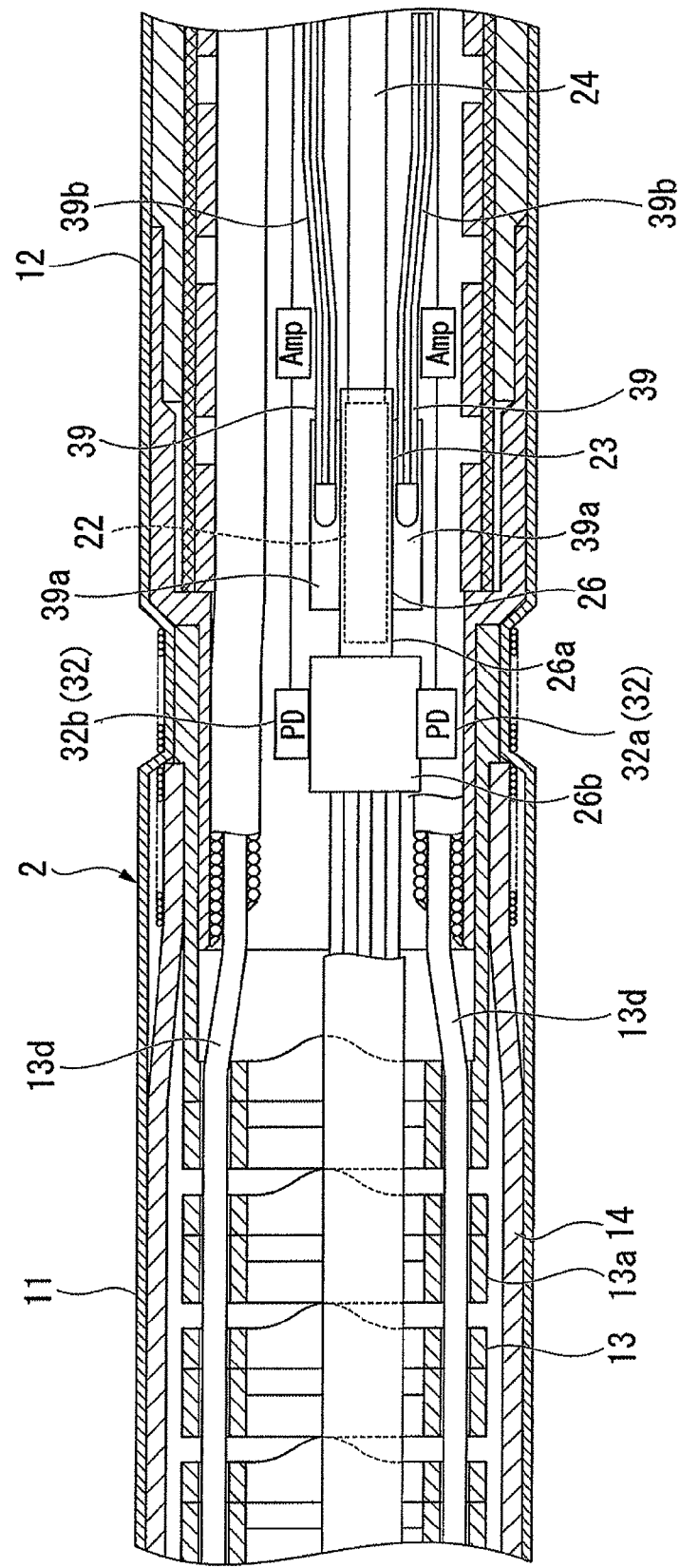
FIG. 12 is a sectional view showing details of a bending portion and a flexible tube portion, in an insertion part of an endoscope apparatus of a fourth modification of the first embodiment.

FIG. 12 shows a fourth modification of this embodiment. As shown in FIG. 12, this modification includes a heat radiation portion 39 which receives the heat generated in the fluorescent member 22, and radiates the heat.

The heat radiation portion 39 has a connection ferrule 39a fixed to the lateral face of the case 26 of the illumination light generating section 23, and heat radiation wires 39b extending to the proximal side from the connection ferrule 39a. The heat radiation wires 39b are, for example, metal, such as copper or iron. In this modification, the heat generated from the fluorescent member 22 is radiated directly to the outside via the case 26, and is conducted and radiated to the heat radiation wire 39b from the connection ferrule 39a of the heat radiation portion 39, whereby the fluorescent member 22 is forcibly cooled. For this reason, the temperature rise of the fluorescent member 22 caused by emission of illumination light can be more effectively suppressed, and degradation of the fluorescent member 22 and decline in the conversion efficiency of the illumination light from the laser light can be more reliably suppressed.

In addition, in the above-described embodiment, the illumination light generating section 23 having the fluorescent member 22 is disposed at a position close to the bending portion 11 on more proximal side than the bending portion 11. That is, the illumination light generating section 23 is arranged at the tip inside the flexible tube portion 12, and the laser diode 21 which is the light source section is installed in the apparatus body part 3 as shown in FIG. 2. However, the positions where the fluorescent member 22 and the light source section are installed are not limited as described above.

For example, in a case where the illumination light generating section 23 having the fluorescent member 22 is provided closer to the proximal side than the bending portion 11 inside the insertion part 2, the light source section may be provided at the following position. That is, the light source section may be provided closer to the proximal side than the fluorescent member 22 within the insertion part, may be provided within the bending operating part 15, or may be provided within the apparatus body part 3.

Moreover, the fluorescent member 22 may be provided within the bending operating part 15. Moreover, in this case, the light source section may be provided closer to the proximal side than the fluorescent member 22 within the bending operating part 15, or may be provided in the apparatus body part 3.

Furthermore, in the above illumination device 1, the fluorescent member 22 may be provided within the apparatus body part 3. That is, the fluorescent member can also be applied to the case of a hard pipe which does not include the bending portion 11.

Furthermore, in this case, the light source section may be provided closer to the proximal side than the fluorescent member 22 within the apparatus body part 3.

(Second Embodiment)

Next, a second embodiment will be described. FIGS. 13 to 16 show the second embodiment. In this embodiment, members common to the members used in the aforementioned embodiment are designated by the same reference numerals, and a description thereof is omitted.

As shown in FIGS. 13 to 16, in an endoscope apparatus 40 of this embodiment, an illumination device 40a includes two illumination portions of a first illumination portion 41 and a second illumination portion 42, and a first light determining portion 43 and a second light determining portion 44 corresponding to the illumination portions, respectively. The first illumination portion 41 includes the laser diode 21, the first light guide 24, the illumination light generating section 23 having the fluorescent member 22, the second light guide 25, the diffuser plate 27, and the optical system 28 for illumination. Additionally, the first light determining portion 43 includes the input-side light determining section 31, and the output-side light determining section 32 having the first optical sensor 32a and second optical sensor 32b.

Additionally, the second illumination portion 42 includes the same configuration as the first illumination portion 41, and, the second light determining portion 44 includes the same configuration as the first light determining portion 43. That is, the second illumination portion 42 includes a laser diode 45, a first light guide 46, an illumination light generating section 48 having a fluorescent member 47, a second light guide 49, a diffuser plate 50, and an optical system 51 for illumination. Additionally, the second light determining portion 44 includes an input-side light determining section 52, and an output-side light determining section 53 having a first optical sensor 53a and second optical sensor 53b. Here, both the laser diode 21 of the first illumination portion 41 and the laser diode 45 of the second illumination portion 42 are connected to the light source driving unit 7 so that currents can be supplied thereto. Additionally, both the illumination light generating section 23 of the first illumination portion 41 and the illumination light generating section 48 of the second illumination portion 42 are provided close to each other on more proximal side than the bending portion 11 in the insertion part 2. However, the illumination light generating section 23 and the illumination light generating section 48 are disposed such that the positions thereof are different from each other in the axial direction of the insertion part 2. In addition, the second light guide 25 of the first illumination portion 41 and the second light guide 49 of the second illumination portion 42 are designed with lengths such that the tips thereof are at almost the same position in the axial direction of the insertion part 2. Additionally, similarly to the first light determining portion 43, a detection signal output from the input-side light determining section 52 of the second light determining portion 44 is transmitted by a signal line 55a, and is amplified by an amplifier 56a. Simultaneously, the detection signal is AD-converted by the AD converter 57a, and is input to the control unit 8. Additionally, individual detection signals output from the first optical sensor 53a and second optical sensor 53b of the output-side light determining section 53 of the second light determining portion 44 are first amplified by amplifiers 53c and 53d, respectively, disposed inside the insertion part 2. Thereafter, the individual detection signals are transmitted by signal lines 55b and 55c, and are further amplified by amplifiers 56b and 56c in the apparatus body part 3. Simultaneously, the individual detection signals are AD-converted by AD converters 57b and 57c, and are input to the control unit 8.

According to the endoscope apparatus 40 of this embodiment, illumination light can be radiated with a larger amount by including two illumination portions, namely the first illumination portion 41 and the second illumination portion 42. Here, the illumination lights of the individual illumination portions are not directly radiated to the outside from the fluorescent members 22 and 47, respectively, and are guided and radiated by the second light guides 25 and 49, respectively. For this reason, the radiation positions of illumination light can be made almost the same by bringing the tips of the second light guides 25 and 49 to almost the same position in the axial direction of the insertion part 2. Simultaneously, the positions of the fluorescent members 22 and 47 in the axial direction of the insertion part 2 can be made different from each other, and the diameter of the insertion part 2 can be made small even if two illumination portions are adopted. In addition, although two illumination portions are adopted in the present embodiment, the invention is not limited thereto. The amount of illumination light can be further increased by adopting three or more illumination portions.

Figure 17:
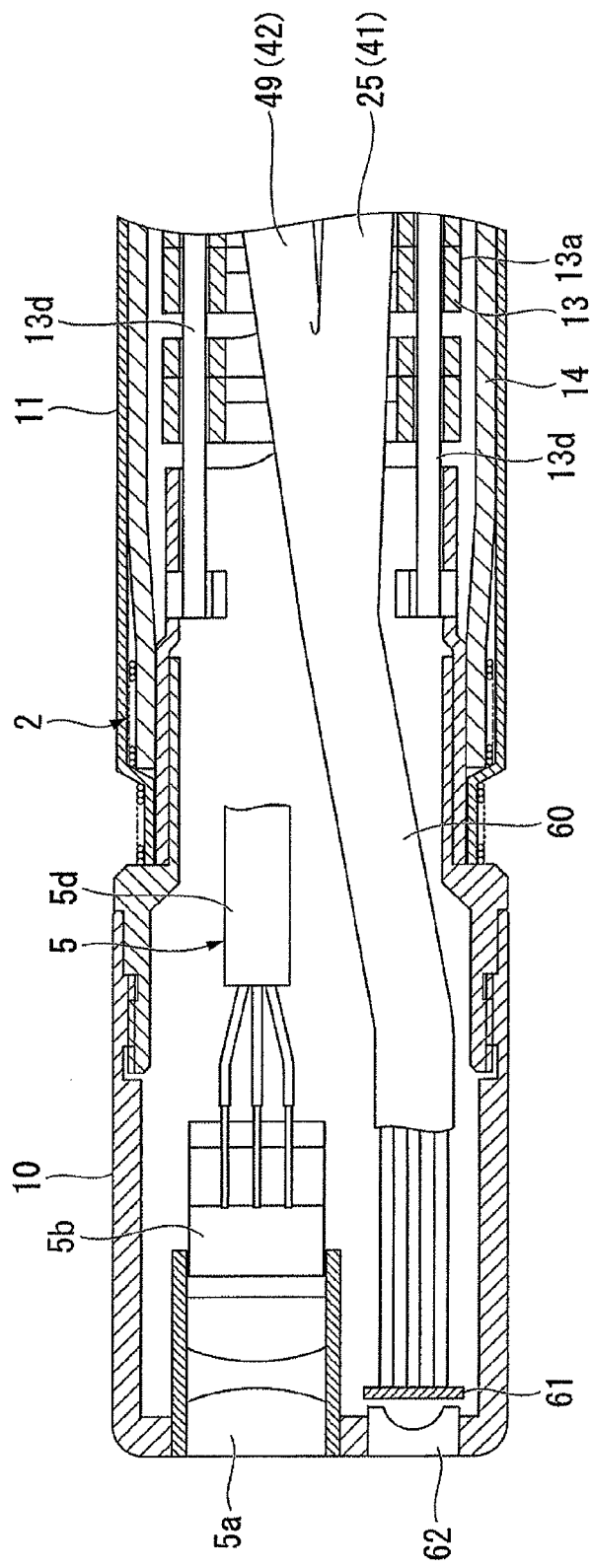
FIG. 17 is a sectional view showing details of a bending portion and a flexible tube portion, in an insertion part of an endoscope apparatus of a modification of the second embodiment.

FIG. 17 shows a modification of this embodiment. As shown in FIG. 17, in an endoscope apparatus of this modification, the second light guide 25 of the first illumination portion 41 and the second light guide 49 of the second illumination portion 42 are bundled as one light guide 60 at the tip. Both individual illumination lights of the first illumination portion 41 and the second illumination portion 42 guided up to the tip by the light guide 60 pass through one diffuser plate 61 and the optical system 62 for illumination, and illuminate the outside. By bundling the second light guides 25 and 49 of the individual illumination portions into one light guide 60 on the distal side as in the endoscope apparatus of this modification, space can be saved, and the diameter of the distal end 10 of the insertion part 2 can be reduced.

As described above, although the embodiments have been described in detail with reference to the drawings, specific configurations are not limited to the embodiments, and various kinds of design changes and the like are also included.

Figure 13:
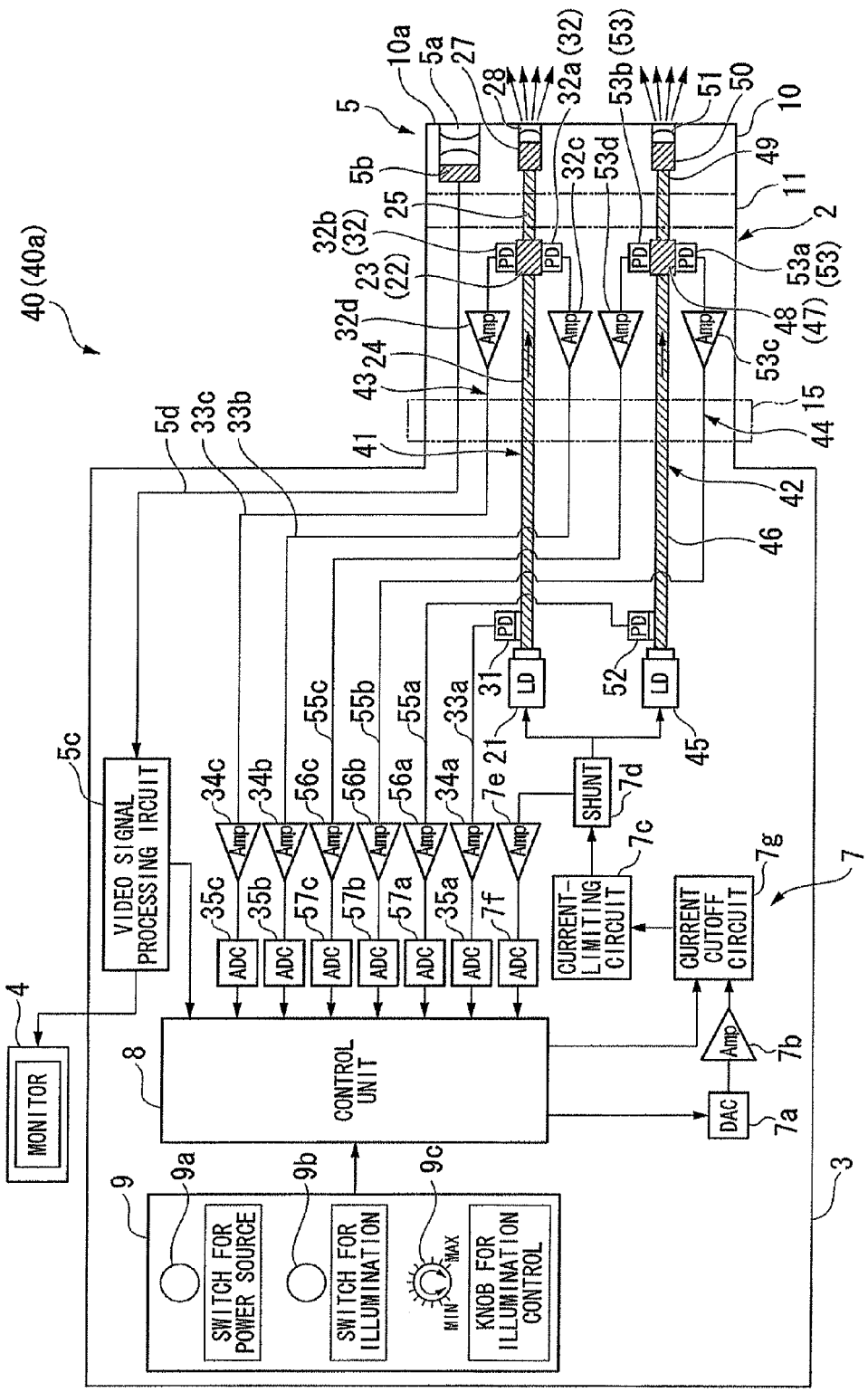
FIG. 13 is an overall configuration view showing an internal configuration of an endoscope apparatus of a second embodiment.
Figure 14:
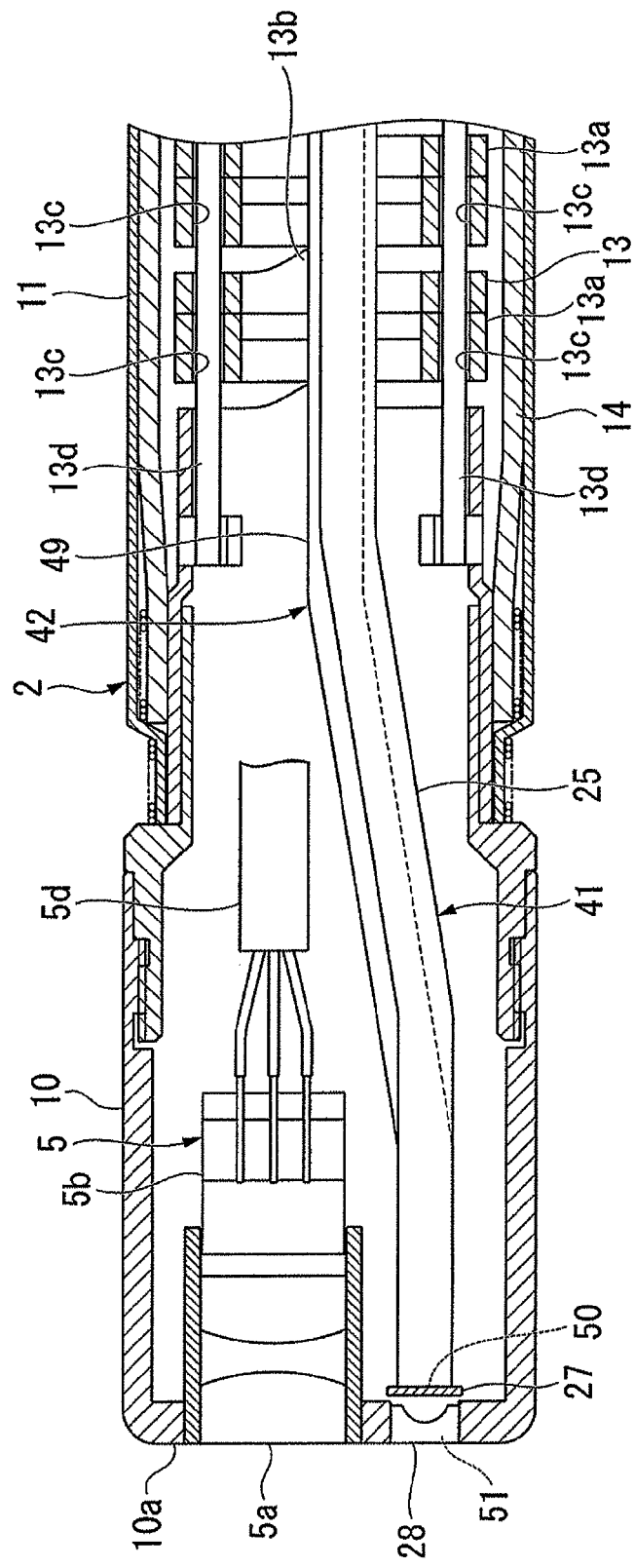
FIG. 14 is a sectional view showing details of a distal end and a bending portion, in an insertion part of the endoscope apparatus of the second embodiment.
Figure 15:
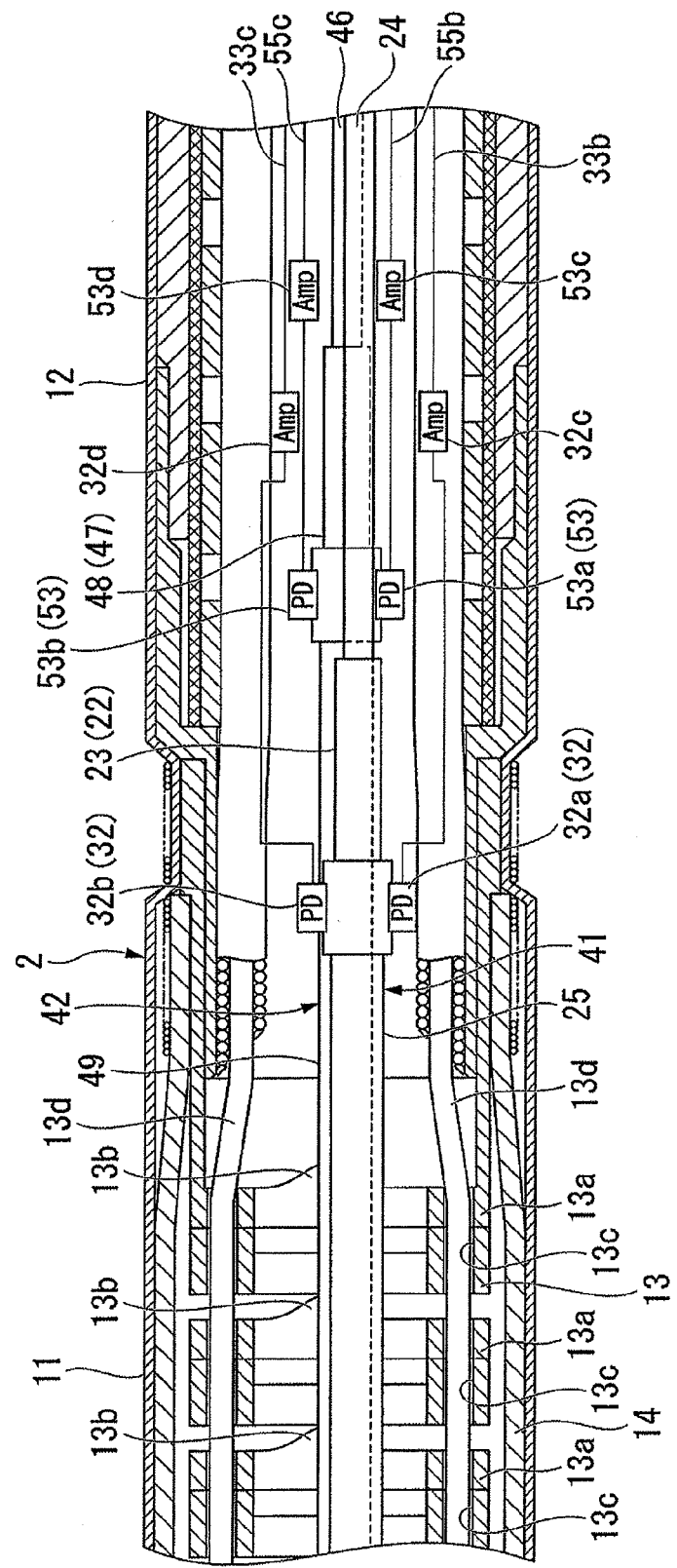
FIG. 15 is a sectional view showing details of the bending portion and a flexible tube portion, in the insertion part of the endoscope apparatus of the second embodiment.
Figure 16:
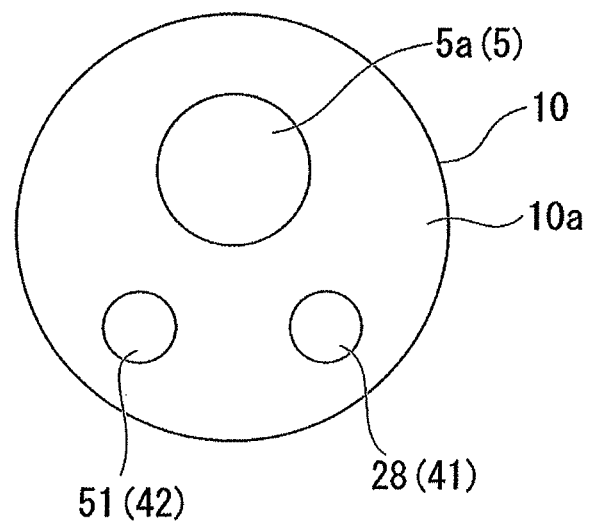
FIG. 16 is a front view of the distal end in the insertion part of the endoscope apparatus of the second embodiment.

In addition, in the above-described embodiment, as shown in FIG. 13, in the first illumination portion 41, the illumination light generating section 23 having the fluorescent member 22 is arranged at a position close to the bending portion 11 on more proximal side than the bending portion 11. That is, the laser diode 21 which is the light source section is installed in the apparatus body part 3. However, the positions where the fluorescent member 22 and the light source section are installed are not limited as described above.

For example, in a case where the illumination light generating section 23 having the fluorescent member 22 is provided closer to the proximal side than the bending portion 11 inside the insertion part 2, the light source section may be provided at the following position. That is, the light source section may be provided closer to the proximal side than the fluorescent member 22 within the insertion part, may be provided within the bending operating part 15, or may be provided within the apparatus body part 3.

Moreover, in the above illumination device 40, the fluorescent member 22 may be provided within the bending operating part 15. Moreover, in this case, the light source section may be provided closer to the proximal side than the fluorescent member 22 within the bending operating part 15, or may be provided in the apparatus body part 3.

Furthermore, the fluorescent member 22 may be provided within the apparatus body part 3. Moreover, in this case, the light source section may be provided closer to the proximal side than the fluorescent member 22 within the apparatus body part 3.

The configuration of the above-described illumination portion 41 can also be similarly applied to the configuration of the second illumination portion 42.

In addition, although the above individual embodiments have described that the insertion part 2 is of a soft type having the flexible tube portion 12, the invention is not limited thereto. The insertion part may be of a hard type having a hard pipe, instead of the flexible tube portion 12.

As described above, although the laser diodes of the individual illumination portions are built into the apparatus body part 3, the invention is not limited thereto. For example, the laser diodes may be built into the bending operating part 15 on the proximal side of the insertion part 2. In addition, the bending operating part 15 is not limited to being provided at the proximal end of the insertion part 2, and may be connected to the apparatus body part 3 as a separate body from the insertion part 2. In this case, the laser diodes may be provided inside the apparatus body part 3 or inside the proximal side of the insertion part 2. Additionally, although the first light transmitting section and the second light transmitting section are constituted by two different light guides, namely the first light guide and the second light guide, the invention is not limited thereto. For example, a fluorescent member may be inserted at an intermediate portion of one light guide, the proximal side of the light guide may be used as the first light transmitting section, and the distal side of the light guide may be used as the second light transmitting section.

Additionally, although the above individual embodiments are configured so as to include the input-side light determining section and the output-side light determining section as light determining portions in correspondence with the individual illumination portions, the invention is not limited thereto. For example, even if a configuration including only any one of the input-side light determining section or the output-side light determining section is adopted, the existence/non-existence of an abnormality of a corresponding component can be detected by the amount of laser light or illumination light determined. Additionally, although the output-side light determining section is configured so as to include the first optical sensor and the second optical sensor, the invention is not limited thereto. For example, only any one of the first optical sensor or the second optical sensor may be included, or the amount of illumination light, which is divided into three or more wavelength regions, may be determined by three or more optical sensors. Moreover, the amount of the total wavelength region of illumination light may be determined by one optical sensor. Additionally, in the output-side light determining section, the first optical sensor may be arranged on the proximal side of the second light transmitting section to detect laser light on the proximal side, and the second optical sensor may be arranged on the distal side of the second light transmitting section to detect illumination light.

According to the illumination device related to the aspect, the excitation light output from the light source section is guided to the first light transmitting section, and excites the fluorescent member. Also, the illumination light with an amount according to the amount of the excitation light is emitted from the fluorescent member, and the illumination light is guided up to the distal side of the second light transmitting section by the second light transmitting section, and is radiated to the outside.

According to the illumination device related to the aspect, the fluorescent member can be arranged closer to the distal side in more proximal side than the bending portion. For this reason, the length of the second light transmitting section disposed from the fluorescent member to the distal side can be minimized, and thereby, attenuation of the illumination light guided by the second light transmitting section can be suppressed to the minimum.

According to the illumination device related to the aspect, the following effects are exhibited even if the bending portion or more distal side than the bending portion in the insertion part is damaged for some reason. That is, since the fluorescent member or the first light transmitting section is provided closer to the proximal side than at least the bending portion of the insertion part, the influence of damage may be suppressed, and leakage of the excitation light can be suppressed. Additionally, since the second light transmitting section is disposed closer to the distal side than the fluorescent member, there is a possibility that the second light transmitting section may be influenced by damage. However, even if the second light transmitting section is damaged, only the guided illumination light leaks out.

Moreover, since the fluorescent member is not provided within the insertion part in a case where the fluorescent member is provided within the bending operating part, or the apparatus body portion, miniaturization of the insertion part is possible.

Moreover, in a case where the fluorescent member is provided at the bending operating part or the apparatus body portion, and the light source section is also provided at the bending operating part or the apparatus body portion, replacement of the fluorescent member and the light source section becomes easy.

According to the illumination device related to the aspect, the illumination light guided by the second light transmitting section is further diffused by the diffuser plate, and is radiated to the outside. For this reason, a wider area can be effectively illuminated.

According to the illumination device related to the aspect, illumination light can be radiated with a larger amount by including a plurality of sets of illumination portions. Here, the illumination light is not radiated directly to the outside from the fluorescent member, and is guided and radiated by the second light transmitting section. For this reason, the radiation positions of illumination light of the plurality of illumination portions can be made approximately the same by bringing the tips of the second light transmitting sections to approximately the same position in the axial direction of the insertion part. Simultaneously, the positions of the fluorescent members in the axial direction of the insertion part can be made different from each other, and the diameter of the insertion part can be made small even if a plurality of illumination portions is adopted.

According to the illumination device related to the aspect, the fluorescent member can be cooled by the heat radiation portion, while radiating excitation light to emit illumination light from the fluorescent member. For this reason, the temperature rise of the fluorescent member caused by the emission of the illumination light can be suppressed, and degradation of the fluorescent member and decline in the conversion efficiency of the illumination light from the excitation light can be suppressed.

According to the illumination device related to the aspect, the amount of the excitation light irradiated to the fluorescent member can be determined by the input-side light determining section. Moreover, on the basis of a detection result, the existence/non-existence of degradation or damage to the light source section and a certain range of the first light transmitting section according to a position to be determined can be detected.

According to the illumination device related to the aspect, the existence/non-existence of degradation or damage can be detected over almost the entire range of the light source section and the first light transmitting section.

According to the illumination device related to the aspect, the amount of the illumination light radiated to the outside can be determined by the output-side light determining section. Moreover, on the basis of a detection result, the existence/non-existence of degradation or damage to the light source section or the first light transmitting section, in addition to the fluorescent member and a certain range of the second light transmitting section according to a position to be determined can be detected.

According to the illumination device related to the aspect, a detection signal is amplified by the amplifier inside the insertion part. Thereby, even in the elongate insertion part, the detection signal can be transmitted to the proximal side, while suppressing an increase in noise and suppressing a decrease in output.

According to the illumination device related to the aspect, the excitation light output from the light source section is suitably guided by the light guide which is the first light transmitting section, and is irradiated to the fluorescent member, whereby the fluorescent member is excited to emit illumination light. Also, the illumination light emitted from the fluorescent member is suitably guided up to the distal side by the light guide which is the second light transmitting section, and is radiated to the outside.

According to the endoscope apparatus related to the aspect, the above illumination device is included. Thereby, there is no possibility that the excitation light may be radiated to the outside, the inside of a subject can be illuminated, and can be observed by the observation portion. Here, the fluorescent member is located closer to the proximal side than at least the bending portion of the insertion part. Thereby, the observation portion and the fluorescent member can be brought to positions which are different from each other in the axial direction of the insertion part, and the heat generated from the fluorescent member can be easily radiated. Additionally, the observation portion can be prevented from being influenced by the heat generated from the fluorescent member.

Advantageous Effects

According to the illumination device and endoscope apparatus related to the aspect, the fluorescent member is provided closer to the proximal side than at least the insertion part, and illumination light is guided by the second light transmitting section. Accordingly, the illumination device and the endoscope apparatus can suppress the radiation of excitation light from the light source section directly to the outside, even if the bending portion or more distal side than the bending portion is damaged.

According to the illumination device and endoscope apparatus related to this embodiment, the fluorescent member is provided closer to the proximal side than at least the bending portion of the insertion part, and illumination light is guided by the second light transmitting section. Accordingly, the illumination device and the endoscope apparatus can suppress radiation of the excitation light from the light source section directly to the outside, even if the bending portion or more distal side than the bending portion is damaged.

The invention claimed is:

1. An endoscope apparatus comprising:
an insertion part having a proximal end and a distal end, with an observation portion at the distal end to observe a subject, a bending portion which is provided more proximal than the distal end, and a tube portion closer to the proximal end than the bending portion, the bending portion has a distal end and a proximal end, wherein in an unbent state of the insertion part, the observation portion, the bending portion, and the tube portion are arranged in that order from the distal end to the proximal end of the insertion part;
a light source section outputting excitation light;
a fluorescent member excited by the excitation light to emit illumination light;
a first light transmitting section disposed between the light source section and the fluorescent member to guide the excitation light output from the light source section to the fluorescent member; and
a second light transmitting section guiding the illumination light emitted from the fluorescent member,
wherein the fluorescent member is fixedly located closer to the proximal end of the bending portion than to the distal end of the bending portion, in an unbent state of said insertion part and wherein the fluorescent member is provided closer to the proximal side of the insertion part than the bending portion, and within the insertion part.

2. The endoscope apparatus according to claim 1, wherein the insertion part further includes a flexible tube portion which is flexible and provided more proximal than the bending portion, and the fluorescent member is provided within the flexible tube portion.

3. The endoscope apparatus according to claim 1, wherein the fluorescent member is provided within an apparatus body portion of the endoscope apparatus.

4. The endoscope apparatus according to claim 3, wherein the light source section is provided within the apparatus body portion.

5. The endoscope apparatus according to claim 1, including a bending operating part which is provided at a proximal side of the insertion part and configured to control bending of the bending portion.

6. The endoscope apparatus according to claim 5, wherein the light source section is provided within the bending operating part.

7. The endoscope apparatus according to claim 1, further comprising a diffuser plate provided on the distal side of the second light transmitting section to diffuse the illumination light guided to the second light transmitting section.

8. The endoscope apparatus according to claim 1, further comprising a plurality of sets of illumination portions having the light source section, the fluorescent member, the first light transmitting section, and the second light transmitting section.

9. The endoscope apparatus according to claim 1,
wherein the fluorescent member is provided with a heat radiation portion which receives and radiates the heat generated in the fluorescent member.

10. The endoscope apparatus according to claim 1, further comprising an input-side light determining section which determines an amount of the excitation light emitted from the light source section and guided to the first light transmitting section, and outputs a detection signal.

11. The endoscope apparatus according to claim 10,
wherein the input-side light determining section is provided in proximity to the fluorescent member.

12. The endoscope apparatus according to claim 11, further comprising an amplifier provided inside the insertion part to amplify the detection signal and transmit the amplified detection signal to the proximal side of the insertion part.

13. The endoscope apparatus according to claim 10, further comprising an amplifier provided inside the insertion part to amplify the detection signal and transmit the amplified detection signal to the proximal side of the insertion part.

14. The endoscope apparatus according to claim 1, further comprising an output-side light determining section which determines the amount of the illumination light emitted from the fluorescent member and guided to the second light transmitting section, and outputs a detection signal.

15. The endoscope apparatus according to claim 14, further comprising an amplifier provided inside the insertion part to amplify the detection signal and transmit the amplified detection signal to the proximal side of the insertion part.

16. The endoscope apparatus according to claim 1,
wherein the first light transmitting section and the second light transmitting section are light guides.

* * * * *